United States Patent [19]

Meyer et al.

[11] 3,948,923

[45] Apr. 6, 1976

[54] PENTAHYDROQUINOLIZINE DERIVATIVES

[75] Inventors: Horst Meyer; Friedrich Bossert, both of Wuppertal-Elberfeld; Wulf Vater, Opladen; Kurt Stoepel, Wuppertal-Vohwinkel, all of Germany

[73] Assignee: Bayer Aktiengesellschaft, Germany

[22] Filed: May 9, 1974

[21] Appl. No.: 468,432

Related U.S. Application Data

[62] Division of Ser. No. 336,477, Feb. 28, 1973, Pat. No. 3,856,798.

[30] Foreign Application Priority Data

Mar. 6, 1972 Germany............................ 2210633

[52] U.S. Cl. 260/294.9; 260/295.5 B; 260/294.8 C; 424/266
[51] Int. Cl.[2] .................................... C07d 213/57
[58] Field of Search ................... 260/294.9, 295.5 B

[56] References Cited

UNITED STATES PATENTS 3,784,600   1/1974   Strandtmann et al........ 260/294.8 C

*Primary Examiner*—Alan L. Rotman

[57] ABSTRACT

1,4-Dihydropyridines bearing carbonyl functions in the 3- and 5-positions, being optionally substituted by lower alkyl in the 6-position, being substituted in the 4-position by lower alkyl, phenyl, substituted phenyl or a heterocyclic group, and being fused through the 1- and 2-positions to a five, six or seven membered cycloalkyl ring, one methylene group of which can be replaced by sulfur, oxygen imino or alkylimino, are anti-hypertensive agents and coronary vessel dilators. The compounds, of which 6-methyl-4-(3-nitrophenyl)-1,2-pentamethylene-1,4-dihydropridine-3,5-dicarboxylic acid 3,5-diethyl ester is a representative embodiment, are prepared through condensation of an ylideneacetoacetic acid ester and a cyclic enamino carbonyl derivative.

7 Claims, No Drawings

PENTAHYDROQUINOLIZINE DERIVATIVES

This is a division of application Ser. No. 336,477 filed Feb. 28, 1973, now U.S. Pat. No. 3,856,798.

DETAILED DESCRIPTION

The present invention pertains to bicyclic derivatives of 1,4-dihydropyridine, to processes for their production and use and to pharmaceutical compositions containing such compounds and useful as antihypertensive agents and coronary vessel dilators.

In particular, the present invention pertains to compounds of the formula:

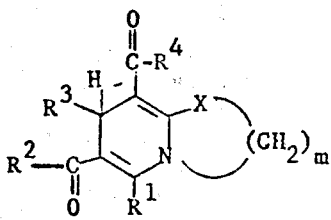

wherein
$R^1$ is hydrogen or lower alkyl;

each of $R^2$ and $R^4$, independent of the other, is lower alkyl or the group -OR', in which R' is a straight-chain, branched or cyclic, saturated or unsaturated, aliphatic hydrocarbyl or oxyhydrocarbyl, the carbon chain of which is optionally interrupted by one or two oxygen atoms;

$R^3$ is a saturated or unsaturated, straight-chain, branched or cyclic hydrocarbyl; aryl optionally carrying 1, 2 or 3 substituents selected from the group consisting of lower alkyl, lower alkoxy, azido, halogen, nitro, nitrile, trifluoromethyl, carbo(lower alkoxy), lower alkylsulfonyl, lower alkylsulfinyl or lower alkylthio; or a member selected from the group consisting of naphthyl, quinolyl, isoquinolyl, pyridyl, pyrimidyl, thienyl, furyl and pyrryl, said member optionally carrying a lower alkyl, lower alkoxy or halogeno substituent;

X is $-CH_2-$, $-NR^5-$ in which $R^5$ is hydrogen or lower alkyl, $-S-$, or $-O-$; and $m$ is 2, 3 or 4.

A preferred class of the foregoing compounds are those of the formula:

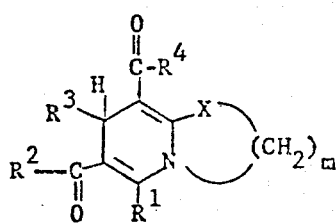

wherein
X is $-O-$, $-S-$, $-CH_2-$ or $-NR^5-$;
$m$ has a value of 2, 3 or 4;
$R^1$ is hydrogen or lower alkyl;
each of $R^2$ and $R^4$, independent of the other, is lower alkyl, lower alkoxy, lower alkoxy(lower alkyl) or lower alkynloxy preferably having 2 to 4 carbon atoms,
$R^3$ is lower alkyl, phenyl, phenyl substituted with from one to three substituents selected from the group consisting of lower alkyl, trifluoromethyl, cyano, halo, nitro and carbo(lower alkoxy); pyridyl; furyl; thienyl; or naphthyl; and
$R^5$ is hydrogen or lower alkyl.

The term lower alkyl denotes a univalent saturated branched or straight hydrocarbon chain containing from 1 to 6 carbon atoms. Representative of such lower alkyl groups are thus methyl, ethyl, propyl, isopropyl, butyl, isobutyl, sec.butyl, tert.butyl, pentyl, isopentyl, neopentyl, tert.pentyl, hexyl, and the like.

The term lower alkenyl denotes a univalent branched or straight hydrocarbon chain containing from 2 to 6 carbon atoms and nonterminal ethylenic unsaturation as, for example, vinyl, allyl, isopropenyl, 2-butenyl, 3-methyl-2-butenyl, 2-pentenyl, 3-pentenyl, 2-hexenyl, 4-hexenyl, and the like.

The term lower alkynyl denotes a univalent branched or straight hydrocarbon chain containing from 2 to 6 carbon atoms and nonterminal acetylenic unsaturation as, for example, ethynyl, 2-propynyl, 4-pentynyl, and the like.

The term lower alkoxy denotes a straight or branched hydrocarbon chain bound to the remainder of the molecule through an ethereal oxygen atom as, for example, methoxy, ethoxy, propoxy, isopropoxy, butoxy, isobutoxy, pentoxy and hexoxy.

The term lower alkylthio denotes a branched or straight hydrocarbon chain bound to the remainder of the molecule through a divalent sulfur as, for example, methylthio, ethylthio, propylthio, isopropylthio, butylthio, and the like.

The term halogen denotes the substituents fluoro, chloro, bromo and iodo.

As indicated, the present invention also pertains to the physiologically acceptable non-toxic acid addition salts of these basic compounds. Such salts include those derived from organic and inorganic acids such as, without limitation, hydrochloric acid, hydrobromic acid, phosphoric acid, sulfuric acid, methane sulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

According to the present invention, the foregoing compounds are prepared by reacting a dicarbonyl compound of the formula:

wherein $R^1$, $R^2$ and $R^3$ are as herein defined, with a cyclic enamino carbonyl compound of the formula:

in which $R^4$, X and $m$ are as herein defined. The condensation proceeds smoothly in good yields simply by heating the two components, generally in the presence of an inert organic solvent such as methanol, ethanol, propanol and similar alkanols, ethers such as dioxane and diethyl ether, glacial acetic acid, pyridine, dimethylformamide, dimethylsulfoxide, acetonitrile and the like. The reaction is conducted at temperatures of from 20° to 250°C, conveniently at the boiling point of the solvent, and while elevated pressure may be utilized, normal atmospheric pressure is generally satisfactory. The reactants are employed in substantially equimolar amounts. The dicarbonyl reagent can be utilized as such or generated in situ by the reaction of an aldehyde of the formula $R^3CHO$ and a $\beta$-dicarbonyl compound of the formula $R^1COCH_2COR^2$.

Many of the dicarbonyl compounds utilized as one of the reactants are known to the art and the others can either be generated in situ as herein described or prepared according to methods well known to the art, see for example Org. Reaction XV, 204 et seq. (1967). Typical of this reactant are the following compounds:

benzylideneacetoacetic acid methyl ester,
ethylideneacetoacetic acid methyl ester,
isopropylideneacetoacetic acid methyl ester,
2-nitrobenzylideneacetoacetic acid methyl ester,
2-nitrobenzylideneacetylacetone,
benzylideneacetylacetone,
3-nitrobenzylideneacetoacetic acid methyl ester,
3-nitrobenzylideneacetoacetic acid propargyl ester,
3-nitrobenzylideneacetoacetic acid allyl ester,
3-nitrobenzylideneacetoacetic acid $\beta$-methoxyethyl ester,
3-nitrobenzylideneacetoacetic acid $\beta$-ethoxyethyl ester,
3-nitrobenzylideneacetoacetic acid isopropyl ester,
3-nitrobenzylideneacetylacetone,
4-nitrobenzylideneacetylacetone,
4-nitrobenzylideneacetoacetic acid $\beta$-propoxyethyl ester,
4-nitrobenzylideneacetoacetic acid n-propyl ester,
3-nitro-6-chlorobenzylideneacetoacetic acid methyl ester,
2-cyanobenzylideneacetoacetic acid methyl ester,
2-cyanobenzylideneacetoacetic acid methyl ester,
2-cyanobenzylideneacetoacetic acid ethyl ester,
2-cyanobenzylidenepropionylacetic acid ethyl ester,
3-cyanobenzylideneacetoacetic acid methyl ester,
3-nitro-4-chlorobenzylideneacetylacetone,
3-nitro-4-chlorobenzylideneacetoacetic acid t-butyl ester,
3-nitro-4-chlorobenzylideneacetoacetic acid methyl ester,
2-nitro-4-methoxybenzylideneacetoacetic acid methyl ester,
2-cyano-4-methylbenzylideneacetoacetic acid ethyl ester,
2-azidobenzylideneacetoacetic acid ethyl ester,
3-azidobenzylideneacetylacetone,
2-methylmercaptobenzylideneacetoacetic acid isopropyl ester,
2-sulphinylmethylbenzylideneacetoacetic acid ethyl ester,
2-sulphonylbenzylidenemethylacetoacetic acid allyl ester,
4-sulphonylmethylbenzylideneacetoacetic acid ethyl ester,
naphth-1-ylideneacetoacetic acid methyl ester,
naphth-1-ylideneacetoacetic acid ethyl ester,
naphth-2-ylideneacetoacetic acid ethyl ester,
2-ethoxynaphth-1-ylideneacetoacetic acid methyl ester,
2-methoxynaphth-1-ylideneacetoacetic acid ethyl ester,
5-bromonaphth-1-ylideneacetoacetic acid methyl ester,
quinol-2-ylmethylideneacetoacetic acid methyl ester,
quinol-3-ylmethylideneacetoacetic acid methyl ester,
quinol-4-ylmethylideneacetoacetic acid ethyl ester,
quinol-8-ylmethylideneacetoacetic acid ethyl ester,
isoquinol-1-ylmethylideneacetoacetic acid methyl ester,
isoquinol-3-ylmethylideneacetoacetic acid methyl ester,
$\alpha$-pyridylmethylideneacetoacetic acid methyl ester,
$\alpha$-pyridylmethylideneacetoacetic acid ethyl ester,
$\alpha$-pyridylmethylideneacetoacetic acid allyl ester,
$\alpha$-pyridylmethylideneacetoacetic acid cyclohexyl ester,
$\beta$-pyridylmethylideneacetoacetic acid $\beta$-methoxyethyl ester,
$\gamma$-pyridylmethylideneacetoacetic acid methyl ester,
6-methyl-$\alpha$-pyridylmethylideneacetoacetic acid ethyl ester,
4,6-dimethoxypyrimid-5-ylmethylideneacetoacetic acid ethyl ester,
then-2-ylmethylideneacetoacetic acid ethyl ester,
fur-2-ylmethylideneacetoacetic acid allyl ester,
pyrr-2-ylthylideneacetoacetic acid methyl ester,
nitrobenzylidenepropionylacetic acid ethyl ester,
$\alpha$-pyridylmethylidenepropionylacetic acid ethyl ester,
$\alpha$-pyridylmethylidenepropionylacetic acid methyl ester,
$\alpha$-pyridylmethylideneacetylacetone,
2-, 3- or 4-methoxybenzylideneacetoacetic acid ethyl ester,
2-, 3- or 4-methoxybenzylideneacetylacetone,
2-methoxybenzylideneacetoacetic acid allyl ester,
2-methoxybenzylideneacetoacetic acid allyl ester,
2-methoxybenzylideneacetoacetic acid propargyl ester,
2-methoxybenzylideneacetoacetic acid $\beta$-methoxyethyl ester,
2-isopropoxybenzylideneacetoacetic acid ethyl ester,
3-butoxybenzylideneacetoacetic acid methyl ester,
3,4,5-trimethoxybenzylideneacetoacetic acid allyl ester,
2-methylbenzylidenepropionylacetic acid methyl ester,
2-, 3- or 4-methylbenzylideneacetoacetic acid ethyl ester,
2-methylbenzylideneacetoacetic acid $\beta$-methoxyethyl ester,
2-methylbenzylideneacetoacetic acid $\beta$-propoxyethyl ester,
2-methylbenzylideneacetylacetone,
3,4-dimethoxy-5-bromobenzylideneacetoacetic acid ethyl ester,
2-, 3- or 4-chlorobenzylideneacetoacetic acid ethyl ester,
2-, 3- or 4-bromobenzylideneacetoacetic acid ethyl ester,
2-, 3- or 4-fluorobenzylideneacetoacetic acid ethyl ester,
2-fluorobenzylideneacetoacetic acid methyl ester,
3-chlorobenzylideneacetylacetone,
3-chlorobenzylidenepropionylacetic acid ethyl ester,
3-chlorobenzylideneacetoacetic acid ethyl ester,
2-chlorobenzylideneacetoacetic acid allyl ester,
2-, 3- or 4-trifluoromethylbenzylideneacetoacetic acid isopropyl ester,
3-trifluoromethylbenzylideneacetoacetic acid methyl ester,
2-carbethoxybenzylideneacetoacetic acid ethyl ester, 3-carbomethoxybenzylideneacetoacetic acid methyl ester,
4-carboisopropoxybenzylideneacetoacetic acid isopropyl ester, and
4-carbomethoxybenzylideneacetoacetic acid allyl ester.

The cyclic enamino carbonyl reactants are similarly known or can be readily produced according to known methods, see for example Barnikow et al., Chem. Ber. 100, 1661 (1967). Typical of these reactants are the following:
2-carbethoxymethylidenepyrrolidine,
2-carbomethoxymethylidenepyrrolidine,
2-carbisopropoxymethylidenepyrrolidine,
2-carballyloxymethylidenepyrrolidine,
2-acetylmethylidenepyrrolidine,
2-carbethoxymethylidenepiperidine,
2-carbomethoxymethylidenepiperidine,
2-acetylmethylidenepiperidine,
2-acetylmethylidenehexahydroazepine,
2-carbethoxymethylidenehexahydroazepine,
2-carbomethoxymethylidenehexahydroazepine,
2-acetylmethylideneimidazolidine,
2-carbethoxymethylideneimidazolidine,
2-carbomethoxymethylideneimidazolidine,
2-carbethoxymethylidene-1-methylimidazolidine,
2-carbisopropoxymethylideneimidazolidine,
2-carballyloxymethylideneimidazolidine,
2-acetylmethylideneoxazolidine,
2-carbomethoxyideneoxazolidine,
2-carbethoxymethylideneoxyzolidine,
2-acetylmethylideneperhydro-1,3-oxazine,
2-carbethoxymethylideneperhydro-1,3-oxazine,
2-acetylmethylidenethiazolidine,
2-carbethoxymethylidenethiazolidine, and
2-carbethoxymethylideneperhydro-1,3-thiazine.

In addition to these mentioned in the examples, the following are also important new compounds:
5-methyl-7-(2-nitrophenyl)-2,3,7-trihydrothiazolo[1,2-a]pyridine-6,8-dicarboxylic acid dimethyl ester,
6-methyl-4-(2-nitrophenyl)-1,2-pentamethylene-1,4-dihydropyridine-3,5-dicarboxylic acid dimethyl ester, and
5-methyl-7-(2-nitrophenyl)-1,2,3,7-tetrahydroindolizine-6,8-dicarboxylic acid 6-methyl ester 8-ethyl ester.

As noted above, the compounds of the present invention demonstrate the ability to reduce blood pressure and to effect a dilation of the coronary vessels. They can accordingly be used where either or both of these effects are desired. Thus upon parenteral, oral or sublingual administration, the compounds produce a distinct and long lasting dilation of the coronary vessels which is intensified by a simultaneous nitrite-like effect of reducing the load on the heart. The effect on heart metabolism is thus one of energy saving. In addition, the compounds lower the blood pressure of normotonic and hypertonic animals and can thus be used as antihypertensive agents. These properties can be conveniently observed in well known laboratory models. Thus for example the coronary vessel dilation effect can be observed by measuring the increase in oxygen saturation in the coronary sinus in the narcotized, heart catheterized dog, as shown in the following table:

| Compounds | I.V. Dose (mg/kg) | $\Delta O_2$ % saturation | Return to normal $O_2$ values (hours) |
|---|---|---|---|
| 5-methyl-7-(2-methylphenyl)-2,3,7-trihydrothiazolo[1,2-a]pyridine-6,8-dicarboxylic acid diethyl ester | 2.0 | 22 | 10 |
| 5-methyl-7-(2-cyanophenyl)-2,3,7-trihydrothiazolo[1,2-a]pyridine-6,8-dicarboxylic acid diethyl ester | 1.0 | 34 | 20 |
| 5-methyl-7-(3-chlorophenyl)-2,3,7-trihydrothiazolo[1,2-a]pyridine-6,8-dicarboxylic acid diethyl ester | 2.0 | 27 | 20 |
| 5-methyl-7-(3-nitrophenyl)-2,3,7-trihydrothiazolo[1,2-a]pyridine-6,8-dicarboxylic acid diethyl ester | 5.0 | 30 | 90 |
| 5-methyl-7-(2-cyanophenyl)-2,3,7-trihydrooxazolo[1,2-a]pyridine-6,8-dicarboxylic acid diethyl ester | 0.5 | 29 | 30 |
| 5-methyl-7-(3-nitrophenyl)-2,3,7-trihydrooxazolo[1,2-a] pyridine-6,8-dicarboxylic acid diethyl ester | 2.0 | 21 | >30 |
| 5-methyl-7-(2-methylphenyl)-2,3,7-trihydrooxazolo[1,2-a]pyridine-6,8-dicarboxylic acid diethyl ester | 5.0 | 20 | 60 |
| 5-methyl-7-(3-chlorophenyl)-2,3,7-trihydrooxazolo[1,2-a]pyridine- | 2.0 | 31 | 20 |

-continued

| Compounds | I.V. Dose (mg/kg) | Δ O₂ % saturation | Return to normal O₂ values (hours) |
|---|---|---|---|
| 6,8-dicarboxylic acid diethyl ester | | | |
| 5-methyl-7-(3-nitrophenyl)-1,2,3,7-tetrahydroimidazolo[1,2-a]-pyridine-6,8-dicarboxylic acid 6-(β-methoxyethyl)-ester 8-ethyl ester | 5.0 | 47 | 45 |
| 5-methyl-7-phenyl-1,2,3,7-tetrahydroimidazolo[1,2-a]-pyridine-6,8-dicarboxylic acid diethyl ester | 3.0 | 11 | 3 |
| 5-methyl-7-(3-nitrophenyl)-1,2,3,7-tetrahydroimidazolo[1,2-a]-pyridine-6,8-dicarboxylic acid diethyl ester | 3.0 | 20 | 45 |
| 5-methyl-7-(2-trifluoromethylphenyl)-1,2,3,7-tetrahydroimidazolo[1,2-a]-pyridine-6,8-dicarboxylic acid diethyl ester | 2.0 | 13 | >180 |
| 5-methyl-7-(α-pyridyl)-1,2,3,7-tetrahydroimidazolo[1,2-a]pyridine-6,8-dicarboxylic acid diethyl ester | 5.0 | 34 | 20 |
| 5-methyl-7-(2-nitrophenyl)-1,2,3,7-tetrahydroimidazolo[1,2-a]-pyridine-6,8-dicarboxylic acid 6-methyl ester 8-ethyl ester | 2.0 | 18 | 30 |
| 4,6-dimethyl-1,2-pentamethylene-1,4-dihydropyridine-3,5-dicarboxylic acid 3-methyl ester 5-ethyl ester | 5.0 | 15 | >60 |
| 6-methyl-4-(3-nitrophenyl)-1,2-pentamethylene-1,4-dihydropyridine-3,5-dicarboxylic acid dimethyl ester | 2.0 | 28 | >180 |
| 6-methyl-4-(3-nitrophenyl)-1,2-pentamethylene-1,4-dihydropyridine-3,5-dicarboxylic acid 3-methyl ester 5-ethyl ester | 0.5 | 22 | 150 |
| 6-methyl-4-(3-nitrophenyl)-1,2-pentamethylene-1,4-dihydropyridine-3,5-dicarboxylic acid 3-ethyl ester 5-methyl ester | 2.0 | 30 | >180 |
| 6-methyl-5-acetyl-4-(3-nitrophenyl)-1,2-pentamethylene-1,4-dihydropyridine-3-carboxylic acid ethyl ester | 3.0 | 30 | 90 |
| 6-methyl-4-(2-cyanophenyl)-1,2-pentamethylene-1,4-dihydropyridine-3,5-dicarboxylic acid 3-methyl ester 5-ethyl ester | 1.0 | 17 | 90 |
| 6-methyl-4-(2-cyanophenyl)-1,2-pentamethylene-1,4-dihydropyridine-3,5-dicarboxylic acid diethyl ester | 1.0 | 21 | >120 |
| 6-methyl-4-(2-chlorophenyl)-1,2-pentamethylene-1,4-dihydropyridine-3,5-dicarboxylic acid 3-methyl ester 5-ethyl ester | 5.0 | 34 | 120 |
| 6-methyl-4-(2-methylphenyl)-1,2-pentamethylene-1,4-dihydropyridine-3,5-dicarboxylic acid | 5.0 | 13 | >90 |

| Compounds | I.V. Dose (mg/kg) | Δ O₂ % saturation | -continued Return to normal O₂ values (hours) |
|---|---|---|---|
| 3-methyl ester 5-ethyl ester | | | |
| 6-methyl-4-(3-chlorophenyl)-1,2-pentamethylene-1,4-dihydropyridine-3,5-dicarboxylic acid diethyl ester | 3.0 | 30 | 150 |
| 6-methyl-4-(2-trifluoromethylphenyl)-1,2-pentamethylene-1,4-dihydropyridine-3,5-dicarboxylic acid 3-methyl ester 5-ethyl ester | 0.3 | 26 | 90 |
| 6-methyl-4-(2-trifluoromethylphenyl)-1,2-pentamethylene-1,4-dihydropyridine-3,5-dicarboxylic acid diethyl ester | 0.2 | 26 | 90 |
| 5-methyl-7-(3-nitrophenyl)-8-acetyl-1,2,3,7-tetrahydroindolizine-6-carboxylic acid ethyl ester | 3.0 | 20 | 3 |
| 5-methyl-7-(3-nitrophenyl)-1,2,3,7-tetrahydroindolizine-6,8-dicarboxylic acid 6-methyl ester 8-ethyl ester | 2.0 | 16 | 90 |
| 5-methyl-7-(2-methylphenyl)-1,2,3,7-tetrahydroindolizine-6,8-dicarboxylic acid diethyl ester | 5.0 | 21 | 90 |
| 6-methyl-8-(2-cyanophenyl)-1,2,3,4,8-pentahydroquinolizine-7,9-dicarboxylic acid diethyl ester | 0.5 | 23 | >60 |
| 5-methyl-6-acetyl-7-(3-nitrophenyl)-2,3,7-trihydrothiazolo[1,2-a]pyridine-8-carboxylic acid ethyl ester | 2.0 | 30 | 20 |
| 5-methyl-7-(3-nitrophenyl)-1,2,3,7-tetrahydroimidazolo[1,2-a]pyridine-6,8-dicarboxylic acid 6-isopropyl ester 8-ethyl ester | 5.0 | 35 | >90 |
| 5-methyl-7-(3-nitrophenyl)-1,2,3,7-tetrahydroimidazolo[1,2-a]pyridine-6,8-dicarboxylic acid 6-propargyl ester 8-ethyl ester | 5.0 | 34 | >30 |

The foregoing values do not necessarily correspond to the lowest dose at which a clearly detectable rise is observed in the oxygen saturation in the coronary sinus. Thus 6-methyl-4-(3-nitrophenyl)-1,2-pentamethylene-1,4-dihydropyridine-3,5-dicarboxylic acid, 6-methyl-4-(2-trifluoromethylphenyl)-1,2-pentamethylene-1,4-dihydropyridine-3,5-dicarboxylic acid 3-methyl ester-5-ethyl ester, and 6-methyl-4-(3-nitrophenyl)-1,2-pentamethylene-1,4-dihydropyridine-3,5-dicarboxylic acid 3-ethyl ester-5-methyl ester produce such a rise at I.V. doses as low as 0.2, 0.3 and 0.5 mg/kg, respectively.

The hypotensive activity of the present compounds can be observed by measuring the blood pressure of hypertensive rats following peoral administration of the compounds. The following table demonstrates the dose which results in at least a 15 mm Hg reduction in blood pressure of such animals:

| Compound | Dose (mg/kg) |
|---|---|
| 5-methyl-7-(2-cyanophenyl)-2,3,7-trihydrooxazolo-[1,2-a]pyridine-6,8-dicarboxylic acid diethyl ester | 1.0 |
| 5-methyl-7-(2-trifluoromethylphenyl)-1,2,3,7-tetrahydroimidazolo[1,2-a]pyridine-6,8-dicarboxylic acid diethyl ester | 3.1 |
| 6-methyl-4-(3-nitrophenyl)-1,2-pentamethylene-1,4-dihydropyridine-3,5-dicarboxylic acid 3-methyl ester 5-ethyl ester | 3.1 |
| 6-methyl-4-(3-nitrophenyl)-1,2-pentamethylene-1,4-dihydropyridine-3,5-dicarboxylic acid 3-ethyl ester 5-methyl ester | 1.0 |
| 6-methyl-4-(2-cyanophenyl)-1,2-pentamethylene-1,4-dihydropyridine-3,5-dicarboxylic acid 3-methyl ester 5-ethyl ester | 3.0 |
| 6-methyl-4-(2-trifluoromethylphenyl)-1,2-penta- | 3.1 |

| Compound | Dose (mg/kg) |
|---|---|
| -continued | |
| methylene-1,4-dihydropyridine-3,5-dicarboxylic acid diethyl ester | |
| 5-methyl-8-acetyl-7-(2-cyanophenyl)-1,2,3,7-tetrahydroindolizine-6-carboxylic acid ethyl ester | 3.1 |
| 6-methyl-8-(2-cyanophenyl)-1,2,3,4,8-pentahydroquinolizine-7,9-dicarboxylic acid diethyl ester | 0.3 |

The toxicity of the compounds is remarkably low, as can be seen from the following toxicities measured in the mouse upon oral administration.

| Compound | Dose (mg/kg) |
|---|---|
| 5-methyl-7-(2-trifluoromethylphenyl)-1,2,3,7-tetrahydroimidazolo[1,2-a]pyridine-6,8-dicarboxylic acid diethyl ester | <3,000 |
| 6-methyl-4-(3-nitrophenyl)-1,2-pentamethylene-1,4-dihydropyridine-3,5-dicarboxylic acid 3-methyl ester 5-ethyl ester | <3,000 |
| 6-methyl-4-(3-nitrophenyl)-1,2-pentamethylene-1,4-dihydropyridine-3,5-dicarboxylic acid 3-ethyl ester 5-methyl ester | <3,000 |
| 6-methyl-4-(2-cyanophenyl)-1,2-pentamethylene-1,4-dihydropyridine-3,5-dicarboxylic acid 3-methyl ester 5-ethyl ester | <3,000 |
| 6-methyl-4-(2-trifluoromethylphenyl)-1,2-pentamethylene-1,4-dihydropyridine-3,5-dicarboxylic acid diethyl ester | <3,000 |
| 5-methyl-8-acetyl-7-(2-cyanophenyl)-1,2,3,7-tetrahydroindolizine-6-carboxylic acid ethyl ester | <3,000 |

In addition to the effect on blood pressure and coronary vessels, the compounds also lower the excitability of the stimulus formation and excitation conduction system within the heart so that an antifibrillation action is observed at therapeutic doses. The tone of the smooth muscle of the vessels is also greatly reduced. This vascular-spasmolytic action can be observed in the entire vascular system as well as in more or less isolated and circumscribed vascular regions such as the central nervous system. In addition, a strong muscular-spasmolytic action is manifested in the smooth muscle of the stomach, the intestinal tract, the urogenital tract and the respiratory system. Finally, there is some evidence that the compounds influence the cholesterol level and lipid level of the blood. These effects complement one another and the compounds are thus highly desirable as pharmaceutical agents to be used in the treatment of hypertension and conditions characterized by a constriction of the coronary blood vessels.

Pharmaceutical compositions for effecting such treatment will contain a major or minor amount, e.g. from 95 to 0.5%, of at least one 1,4-dihydropyridine as herein defined in combination with a pharmaceutical carrier, the carrier comprising one or more solid, semi-solid or liquid diluent, filler and formulation adjuvant which is non-toxic, inert and pharmaceutically acceptable. Such pharmaceutical compositions are preferably in dosage unit form; i.e. physically discrete units containing a predetermined amount of the drug corresponding to a fraction or multiple of the dose which is calculated to produce the desired therapeutic response. The dosage units can contain one, two, three, four or more single doses or, alternatively, one-half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the daily dose will be from about 0.05 to about 10 mg/kg, preferably 0.1 to 5.0 mg/kg, when administered parenterally and from about 1 to about 100 mg/kg, preferably 5 to 50 mg/kg, when administered orally. In some instances a sufficient therapeutic effect can be obtained at lower doses while in others, larger doses will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coating to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

The following examples will serve to further typify the nature of the present invention through the presentation of specific embodiments. These examples should not be construed as a limitation on the scope of the invention since the subject matter regarded as the invention is set forth in the appended claims.

EXAMPLE 1

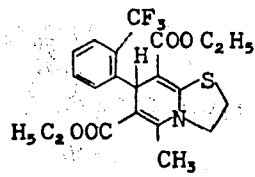

Upon boiling a solution of 9.5 g of 2-trifluoromethylbenzylideneacetoacetic acid ethyl ester and 6.2 g of 2-carbethoxymethylidenethiazolidine in 60 ml of ethanol for 8 hours, 5-methyl-7-(2-trifluoromethylphenyl)-2,3,7-trihydrothiazolo[1,2-a]-pyridine-6,8-dicarboxylic acid diethyl ester of melting point 107° (ethyl acetate/petroleum ether) is obtained.

Yield: 57% of theory.

EXAMPLE 2

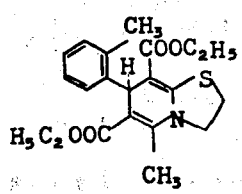

Upon heating a solution of 7.8 g of 2-methylbenzylideneacetoacetic acid ethyl ester and 5.8 g of 2-carbethoxymethylidenethiazolidine in 50 ml of isopropanol for 10 hours, 5-methyl-7-(2-methylphenyl)-2,3,7-trihydrothiazolo[1,2-a]-pyridine-6,8-dicarboxylic acid diethyl ester of melting point 158° (alcohol) is obtained.

Yield: 66% of theory.

EXAMPLE 3

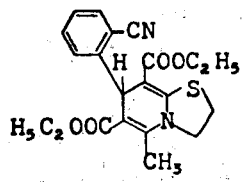

Heating a solution of 8.1 g of 2-cyanobenzylideneacetoacetic acid ethyl ester and 5.7 g of 2-carbethoxymethylidenethiazolidine in 60 ml of ethanol for 6 hours yields 5-methyl-7-(2-cyanophenyl)-2,3,7-trihydrothiazolo[1,2-a]pyridine-6,8-dicarboxylic acid diethyl ester of melting point 206° (ethanol).

Yield: 84% of theory.

EXAMPLE 4

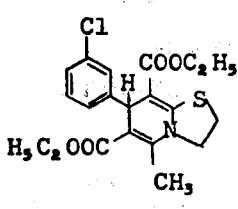

Upon heating a solution of 8.4 g of 3-chlorobenzylideneacetoacetic acid ethyl ester and 5.7 g of 2-carbethoxymethylidenethiazolidine in 50 ml of ethanol for 6 hours, 5-methyl-7-(3-chlorophenyl)-2,3,7-trihydrothiazolo[1,2-a]pyridine-6,8-dicarboxylic acid diethyl ester of melting point 109° (ethyl acetate/petroleum ether) is obtained.

Yield: 71% of theory.

EXAMPLE 5

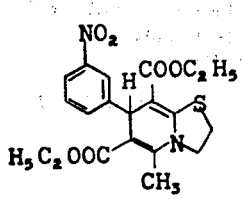

Boiling a solution of 8.8 g of 3-nitrobenzylideneacetoacetic acid ethyl ester and 5.7 g of 2-carbethoxymethylidenethiazolidine in 50 ml of ethanol for 6 hours yields 5-methyl-7-(3-nitrophenyl)-2,3,7trihydrothiazolo[1,2-a]pyridine-6,8-dicarboxylic acid diethyl ester of melting point 143° (ethanol).

Yield: 68% of theory.

EXAMPLE 6

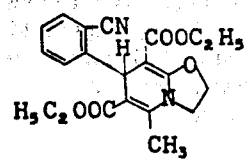

Heating a solution of 8.1 g of 2-cyanobenzylideneacetoacetic acid ethyl ester and 5.2 g of 2-carbethoxymethylideneoxazolidine in 50 ml of ethanol for 8 hours yields 5-methyl-7-(2-cyanophenyl)-2,3,7-trihydrooxazolo[1,2-a]pyridine-6,8-dicarboxylic acid diethyl ester of melting point 199° (alcohol).

Yield: 51% of theory.

EXAMPLE 7

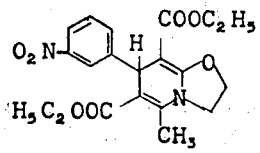

Upon boiling a solution of 8.8 g of 3-nitrobenzylideneacetoacetic acid ethyl ester and 5.2 g of 2-carbethoxymethylideneoxazolidine in 60 ml of glacial acetic acid for 6 hours, 5-methyl-7-(3-nitrophenyl)-2,3,7-trihydrooxazolo[1,2-a]pyridine-6,8-dicarboxylic acid diethyl ester of melting point 179° (ethanol) is obtained.

Yield: 62% of theory.

EXAMPLE 8

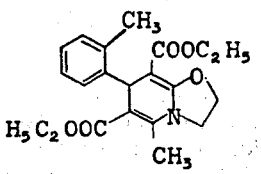

Upon heating a solution of 7.7 g of 2-methylbenzylideneacetoacetic acid ethyl ester and 5.2 g of 2-carbethoxymethylideneoxazolidine in 50 ml of ethanol for 8 hours, 5-methyl-7-(2-methylphenyl)-2,3,7-trihydrooxazolo[1,2-a]pyridine-6,8-dicarboxylic acid diethyl ester of melting point 145° (ethyl acetate/petroleum ether) is obtained.

Yield: 59% of theory.

EXAMPLE 9

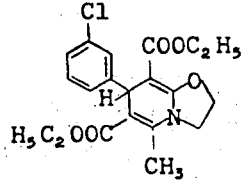

Boiling a solution of 8.4 g of 3-chlorobenzylideneacetoacetic acid ethyl ester and 5.2 g of 2-carbethoxymethylideneoxazolidine in 50 ml of glacial acetic acid for 8 hours yields 5-methyl-7-(3-chlorophenyl)-2,3,7-trihydrooxazolo[1,2-a]-pyridine-6,8-dicarboxylic acid diethyl ester of melting point 110° (ethyl acetate/petroleum ether).

Yield: 66% of theory.

EXAMPLE 10

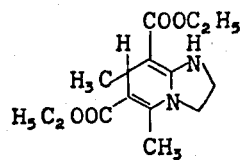

Upon heating a solution of 6 g of ethylideneacetoacetic acid ethyl ester and 6 g of 2-carbethoxymethylideneimidazolidine in 50 ml of ethanol for 10 hours, 5,7-dimethyl-1,2,3,7-tetrahydroimidazolo[1,2-a]pyridine-6,8-dicarboxylic acid diethyl ester of melting point 138° (ethanol) is obtained.

Yield: 58% of theory.

EXAMPLE 11

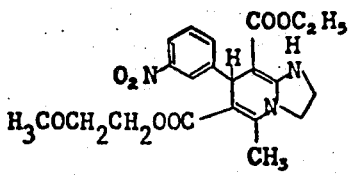

Upon heating a solution of 9.8 g of 3-nitrobenzylideneacetoacetic acid β-methoxyethyl ester and 5.2 g of 2-carbethoxymethylideneimidazolidine in 60 ml of alcohol for 6 hours, 5-methyl-7-(3-nitrophenyl)-1,2,3,7-tetrahydroimidazolo[1,2-a]pyridine-6,8-dicarboxylic acid 6-(β-methoxyethyl) ester 8-ethyl ester of melting point 126°–127° (alcohol) is obtained.

Yield: 63% of theory.

EXAMPLE 12

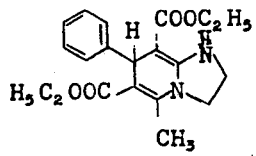

Upon heating a solution of 5.3 g of benzaldehyde, 6.5 g of acetoacetic acid ethyl ester and 7.8 g of 2-carbethoxymethylideneimidazolidine in 50 ml of ethanol for 6 hours, 5-methyl-7-phenyl-1,2,3,7-tetrahydroimidazolo[1,2-a]pyridine-6,8-dicarboxylic acid diethyl ester of melting point 165° (alcohol) is obtained.

Yield: 81% of theory.

EXAMPLE 13

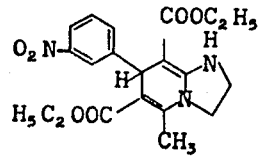

Heating a solution of 8.8 g of 3-nitrobenzylideneacetoacetic acid ethyl ester and 5.2 g of 2-carbethoxymethylideneimidazolidine in 50 ml of alcohol for 6 hours yields 5-methyl-7-(3-nitrophenyl)-1,2,3,7-tetrahydroimidazolo[1,2-a]pyridine-6,8-dicarboxylic acid diethyl ester of melting point 159°–60° (alcohol/-dimethylformamide).

Yield: 68% of theory.

EXAMPLE 14

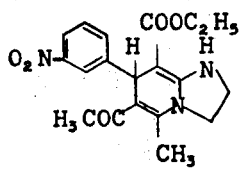

Boiling a solution of 7.8 g of 3-nitrobenzylideneacetylacetone and 5.2 g of 2-carbethoxymethylideneimidazolidine in 50 ml of glacial acetic acid for 6 hours yields 5-methyl-6-acetyl-7-(3-nitrophenyl)-1,2,3,7-tetrahydroimidazolo[1,2-a]pyridine-8-carboxylic acid ethyl ester of melting point 155° (ethanol).

Yield: 54% of theory.

EXAMPLE 15

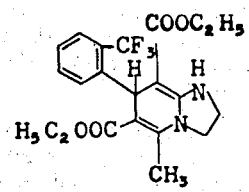

Upon heating a solution of 9.5 g of 2-trifluoromethylbenzylideneacetoacetic acid ethyl ester and 5.2 g of 2-carbethoxymethylideneimidazolidine in 50 ml of ethanol for 6 hours, 5-methyl-7-(2-trifluoromethylphenyl)-1,2,3,7-tetrahydroimidazolo[-1,2-a]pyridine-6,8-dicarboxylic acid diethyl ester of melting point 137° (alcohol) is obtained.

Yield: 63% of theory.

EXAMPLE 16

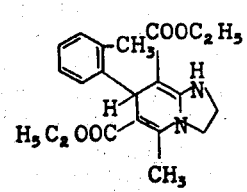

Boiling a solution of 7.7 g of 2-methylbenzylideneacetoacetic acid ethyl ester and 5.2 g of 2-carbethoxymethylideneimidazolidine in 50 ml of ethanol for 10 hours yields 5-methyl-7-(2-methylphenyl)-1,2,3,7-tetrahydroimidazolo[1,2-a]pyridine-6,8-dicarboxylic acid diethyl ester of melting point 202° (alcohol).

Yield: 69% of theory.

EXAMPLE 17

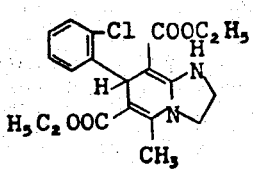

Boiling a solution of 8.4 g of 2-chlorobenzylideneacetoacetic acid ethyl ester and 5.2 g of 2-carbethoxymethylideneimidazolidine in 50 ml of ethanol for 8 hours yields 5-methyl-7-(2-chlorophenyl)-1,2,3,7-tetrahydroimidazolo[1,2-a]pyridine-6,8-dicarboxylic acid diethyl ester of melting point 198° (alcohol).

Yield: 59% of theory.

EXAMPLE 18

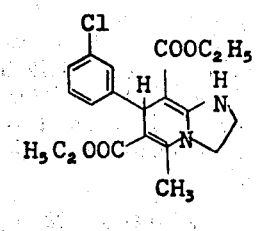

Upon heating a solution of 8.4 g of 3-chlorobenzylideneacetoacetic acid ethyl ester and 5.2 g of 2-carbethoxymethylideneimidazolidine in 50 ml of ethanol for 8 hours, 5-methyl-7-(3-chlorophenyl)-1,2,3,7-tetrahydroimidazolo[1,2-a]pyridine-6,8-dicarboxylic acid diethyl ester of melting point 137° (alcohol) is obtained.

Yield: 60% of theory.

EXAMPLE 19

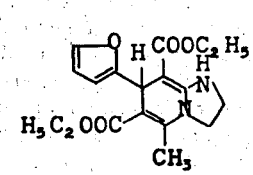

Boiling a solution of 6.9 g of 2-furfurylideneacetoacetic acid ethyl ester and 5.2 g of 2-carbethoxymethylideneimidazolidine in 50 ml of ethanol for 8 hours yields 5-methyl-7-(2-furyl)-1,2,3,7-tetrahydroimidazolo[1,2-a]pyridine-6,8-dicarboxylic acid diethyl ester of melting point 164° (ethanol).

Yield: 65% of theory.

EXAMPLE 20

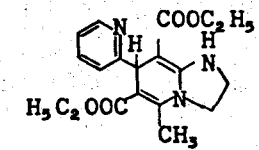

Upon heating a solution of 5.4 g of pyridin-2-aldehyde, 6.5 g of acetoacetic acid ethyl ester and 5.2 g of 2-carbethoxymethylideneimidazolidine in 50 ml of ethanol for 6 hours, 5-methyl-7-(α-pyridyl)-1,2,3,7-tetrahydroimidazolo[1,2-a]pyridine-6,8-dicarboxylic acid diethyl ester of melting point 191° (isopropanol) is obtained.

Yield: 46% of theory.

EXAMPLE 21

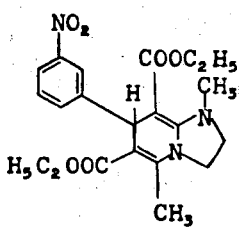

Boiling a solution of 8.7 g of 3-nitrobenzylideneacetoacetic acid ethyl ester and 5.2 g of 2-carbethoxymethylidene-1-methylimidazolidine in 50 ml of alcohol for 6 hours yields 1,5-dimethyl-7-(3-nitrophenyl)-1,2,3,7-tetrahydroimidazolo]1,2-a]pyridine-6,8-dicarboxylic acid diethyl ester (oil).
Yield: 69% of theory.

EXAMPLE 22

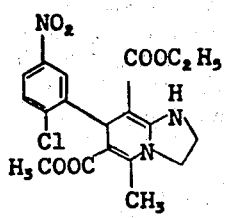

Upon heating a solution of 7.1 g of 3-nitro-6-chlorobenzylideneacetoacetic acid methyl ester and 3.9 g of 2-carbethoxymethylideneimidazolidine in 50 ml of ethanol for 8 hours, 5-methyl-7-(3-nitro-6-chlorophenyl)-1,2,3,7-tetrahydroimidazolo-[1,2-a]pyridine-6,8-dicarboxylic acid 6-methyl ester 8-ethyl ester of melting point 182° (alcohol) is obtained.
Yield: 75% of theory.

EXAMPLE 23

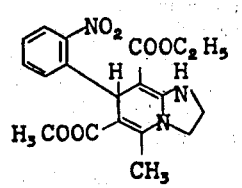

Upon boiling a solution of 8.3 g of 2-nitrobenzylideneacetoacetic acid methyl ester and 5.2 g of 2-carbethoxymethylideneimidazolidine in 50 ml of ethanol for 6 hours, 5-methyl-7-(2-nitrophenyl)-1,2,3,7-tetrahydroimidazolo[1,2-a]pyridine-6,8-dicarboxylic acid 6-methyl ester 8-ethyl ester of melting point 185° is obtained.

EXAMPLE 24

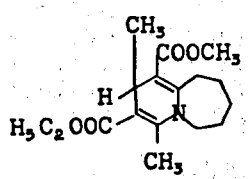

Upon boiling a solution of 7.8 g of ethylideneacetoacetic acid ethyl ester and 8.5 g of 2-carbomethoxymethylidenehexahydroazepine in 50 ml of alcohol for 6 hours, 4,6-dimethyl-1,2-pentamethylene-1,4-dihydropyridine-3,5-dicarboxylic acid 3-methyl ester 5-ethyl ester of melting point 70° (ethyl acetate/petroleum) is obtained.
Yield: 57% of theory.

EXAMPLE 25

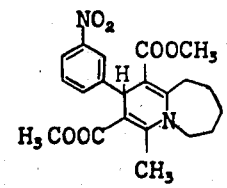

Upon boiling a solution of 8.3 g of 3-nitrobenzylideneacetoacetic acid methyl ester and 5.7 g of 2-carbomethoxymethylidenehexahydroazepine in 50 ml of glacial acetic acid for 8 hours, 6-methyl-4-(3-nitrophenyl)-1,2-pentamethylene-1,4-dihydropyridine-3,5-dicarboxylic acid dimethyl ester of melting point 98° (ethyl acetate/petroleum ether) is obtained.
Yield: 68% of theory.

EXAMPLE 26

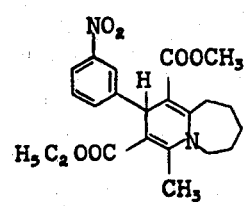

Heating a solution of 8.8 g of 3-nitrobenzylideneacetoacetic acid ethyl ester and 5.6 g of 2-carbomethoxymethylidenehexahydroazepine in 50 ml of ethanol for 6 hours yields 6-methyl-4-(3-nitrophenyl)-1,2-pentamethylene-1,4-dihydropyridine-3,5-dicarboxylic acid 3-methyl ester 5-ethyl ester of melting point 75° (ethyl acetate/petroleum ether).
Yield: 56% of theory.

EXAMPLE 27

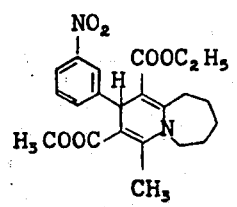

After boiling a solution of 8.3 g of 3-nitrobenzylideneacetoacetic acid methyl ester and 6.1 g of 2-carbethoxymethylidenehexahydroazepine in 50 ml of alcohol for 8 hours, 6-methyl-4-(3-nitrophenyl)-1,2-pentamethylene-1,4-dihydropyridine-3,5-dicarboxylic acid 3-ethyl ester 5-methyl ester of melting point 85°C (ethyl acetate/petroleum ether) is obtained.
Yield: 62% of theory.

EXAMPLE 28

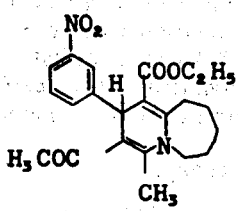

Upon heating a solution of 7.6 g of 3-nitrobenzaldehyde, 5.0 g of acetylacetone and 9.1 g of 2-carbethoxymethylidenehexahydroazepine in 50 ml of ethanol for 8 hours, 6-methyl-5-acetyl-4-(3-nitrophenyl)-1,2-pentamethylene-1,4-dihydropyridine-3-carboxylic acid ethyl ester of melting point 91° (alcohol/water) is obtained.

Yield: 48% of theory.

EXAMPLE 29

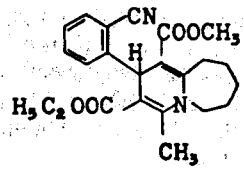

Upon boiling a solution of 8.1 g of 2-cyanobenzylideneacetoacetic acid ethyl ester and 5.6 g of 2-carbomethoxymethylidenehexahydroazepine in 50 ml of ethanol for 8 hours, 6-methyl-4-(2-cyanophenyl)-1,2-pentamethylene-1,4-dihydropyridine-3,5-dicarboxylic acid 3-methyl ester 5-ethyl ester of melting point 154° (alcohol) is obtained.

Yield: 61% of theory.

EXAMPLE 30

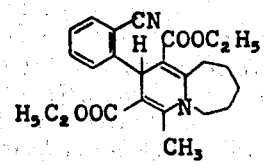

Boiling a solution of 8.1 g of 2-cyanobenzylideneacetoacetic acid ethyl ester and 6.1 g of 2-carbethoxymethylidenehexahydroazepine in 50 ml of ethanol for 6 hours yields 6-methyl-4-(2-cyanophenyl)-1,2-pentamethylene-1,4-dihydropyridine-3,5-dicarboxylic acid diethyl ester of melting point 134° (ethyl acetate/petroleum ether).

Yield: 54% of theory.

EXAMPLE 31

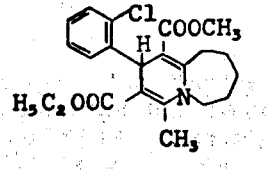

Upon boiling a solution of 8.4 g of 2-chlorobenzylideneacetoacetic acid ethyl ester and 5.6 g of 2-carbomethoxymethylidenehexahydroazepine in 50 ml of ethanol for 6 hours, 6-methyl-4-(2-chlorophenyl)-1,2-pentamethylene-1,4-dihydropyridine-3,5-dicarboxylic acid 3-methyl ester 5-ethyl ester of melting point 123° (ethanol) is obtained.

Yield: 50% of theory.

EXAMPLE 32

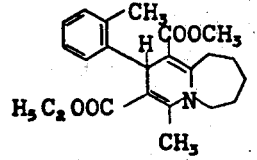

Upon heating a solution of 7.7 g of 2-methylbenzylideneacetoacetic acid ethyl ester and 5.6 g of 2-carbomethoxymethylidenehexahydroazepine in 50 ml of ethanol for 8 hours, 6-methyl-4-(2-methylphenyl)-1,2-pentamethylene-1,4-dihydropyridine-3,5-dicarboxylic acid 3-methyl ester 5-ethyl ester of melting point 130° (alcohol) is obtained.

Yield: 74% of theory.

EXAMPLE 33

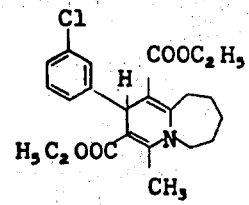

Boiling a solution of 8.4 g of 3-chlorobenzylideneacetoacetic acid ethyl ester and 6.1 g of 2-carbethoxymethylidenehexahydroazepine in 50 ml of glacial acetic acid for 6 hours yields 6-methyl-4-(3-chlorophenyl)-1,2-pentamethylene-1,4-dihydropyridine-3,5-dicarboxylic acid diethyl ester of melting point 100° (ethyl acetate/petroleum ether).

Yield: 65% of theory.

EXAMPLE 34

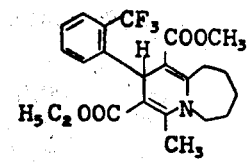

After boiling a solution of 9.1 g of 2-trifluoromethylbenzylideneacetoacetic acid ethyl ester and 5.6 g of 2-carbomethoxymethylidenehexahydroazepine in 50 ml of ethanol for 8 hours, 6-methyl-4-(2-trifluoromethylphenyl)-1,2-pentamethylene-1,4-dihydropyridine-3,5-dicarboxylic acid 3-methyl ester 5-ethyl ester of melting point 111° (ethyl acetate/petroleum ether) is obtained.

Yield: 76% of theory.

EXAMPLE 35

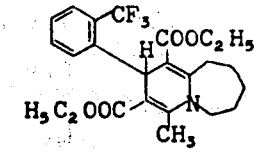

Heating a solution of 9.1 g of 2-trifluoromethylbenzylideneacetoacetic acid ethyl ester and 6.1 g of 2-carbethoxymethylidenehexahydroazepine in 50 ml of ethanol for 10 hours yields 6-methyl-4-(2-trifluoromethylphenyl)-1,2-pentamethylene-1,4-dihydropyridine-3,5-dicarboxylic acid diethyl ester of melting point 104° (alcohol/water).

Yield: 71% of theory.

EXAMPLE 36

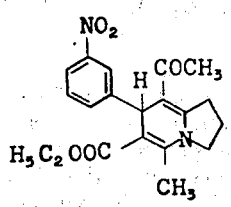

Boiling a solution of 8.8 g of 3-nitrobenzylideneacetoacetic acid ethyl ester and 4.6 g of 2-acetylmethylidenepyrrolidine in 50 ml of ethanol for 6 hours yields 5-methyl-7-(3-nitrophenyl)-8-acetyl-1,2,3,7-tetrahydroindolizine-6-carboxylic acid ethyl ester of melting point 161° (isopropanol).

Yield: 72% of theory.

EXAMPLE 37

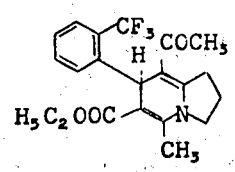

Upon heating a solution of 9.4 g of 2-trifluoromethylbenzylideneacetoacetic acid ethyl ester and 4.6 g of 2-acetylmethylidenepyrrolidine in 50 ml of glacial acetic acid for 8 hours, 5-methyl-8-acetyl-7-(2-trifluoromethylphenyl)-1,2,3,7-tetrahydroindolizine-6-carboxylic acid ethyl ester of melting point 126° (ethyl acetate/petroleum ether) is obtained.

Yield: 49% of theory.

EXAMPLE 38

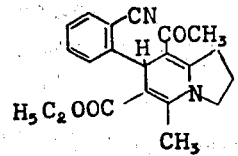

Upon boiling a solution of 8.1 g of 2-cyanobenzylideneacetoacetic acid ethyl ester and 4.6 g of acetylmethylidenepyrrolidine in 50 ml of ethanol for 6 hours, 5-methyl-8-acetyl-7-(2-cyanophenyl)-1,2,3,7-tetrahydroindolizine-6-carboxylic acid ethyl ester of melting point 167° (ethanol) is obtained.

Yield: 59% of theory.

EXAMPLE 39

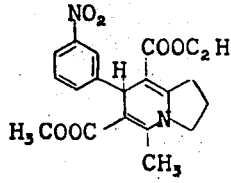

Upon boiling a solution of 8.3 g of 3-nitrobenzylideneacetoacetic acid methyl ester and 5.6 g of 2-carbethoxymethylidenepyrrolidine in 50 ml of glacial acetic acid for 8 hours, 5-methyl-7-(3-nitrophenyl)-1,2,3,7-tetrahydroindolizine-6,8-dicarboxylic acid 6-methyl ester 8-ethyl ester of melting point 120° (ethanol) is obtained.

Yield: 73% of theory.

EXAMPLE 40

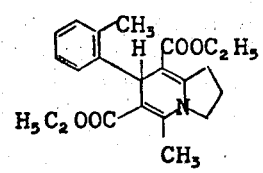

Upon boiling a solution of 7.7 g of 2-methylbenzylideneacetoacetic acid ethyl ester and 5.6 g of carbethoxymethylidenepyrrolidine in 50 ml of ethanol for 8 hours, 5-methyl-7-(2-methylphenyl)-1,2,3,7-tetrahydroindolizine-6,8-dicarboxylic acid diethyl ester of melting point 148° (alcohol) is obtained.

Yield: 62% of theory.

EXAMPLE 41

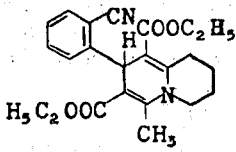

Upon heating a solution of 8.1 g of 2-cyanobenzylideneacetoacetic acid ethyl ester and 5.6 g of 2-carbethoxymethylidenepiperidine in 50 ml of ethanol for 6 hours, 6-methyl-8-(2-cyanophenyl)-1,2,3,4,8-pentahydroquinolizine-7,9-dicarboxylic acid diethyl ester of melting point 142° (ethyl acetate/petroleum ether) is obtained.

Yield: 59% of theory.

EXAMPLE 42

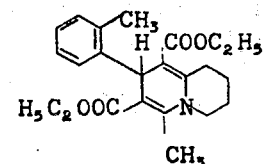

Boiling a solution of 7.7 g of 2-methylbenzylideneacetoacetic acid ethyl ester and 5.6 g of 2-carbethoxymethylidenepiperidine in 50 ml of ethanol for 12 hours yields 6-methyl-8-(2-methylphenyl)-1,2,3,4,8-pentahydroquinolizine-7,9-dicarboxylic acid diethyl ester of melting point 106° (ethyl acetate/petroleum ether).

Yield: 75% of theory.

EXAMPLE 43

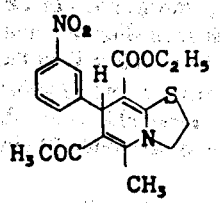

Upon boiling a solution of 7.8 g of 3-nitrobenzylideneacetylacetone and 5.7 g of 2-carbethoxymethylidenethiazolidine in 60 ml of ethanol for 7 hours, 5-methyl-6-acetyl-7-(3-nitrophenyl)-2,3,7-trihydrothiazolo[1,2-a]pyridine-8-carboxylic acid ethyl ester of melting point 152° (ethyl acetate/petroleum ether) is obtained.

Yield: 59% of theory.

EXAMPLE 44

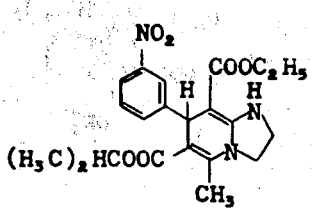

Boiling a solution of 9.2 g of 3-nitrobenzylideneacetoacetic acid isopropyl ester and 5.2 g of 2-carbethoxymethylideneimidazolidine in 60 ml of ethanol for 2 hours yields 5-methyl-7-(3-nitrophenyl)-1,2,3,7-tetrahydroimidazolo[1,2-a]pyridine-6,8-dicarboxylic acid 6-isopropyl ester 8-ethyl ester of melting point 136° (ethanol).

Yield: 65% of theory.

EXAMPLE 45

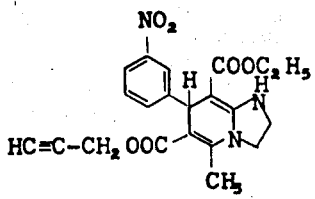

Heating a solution of 9.1 g of 3-nitrobenzylideneacetoacetic acid propargyl ester and 5.2 g of 2-carbethoxymethylideneimidazolidine in 60 ml of ethanol for 6 hours yields 5-methyl-7-(3-nitrophenyl)-1,2,3,7-tetrahydroimidazolo[1,2-a]pyridine-6,8-dicarboxylic acid 6-propargyl ester 8-ethyl ester of melting point 153° (ethanol).

Yield: 54% of theory.

EXAMPLE 46

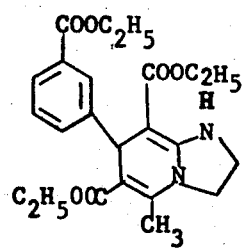

Heating a solution of 9.7 g of 3-carbethoxybenzylideneacetoacetic acid ethyl ester and 5.2 g of 2-carbethoxymethylideneimidazolidine in 60 ml of ethanol for 6 hours yields 5-methyl-7-(3-carbethoxyphenyl)-1,2,3,7-tetrahydroimidazolo[1,2-a]pyridine-6,8-dicarboxylic acid diethyl ester of melting point 149°C (ethanol).

Yield: 69% of theory.

EXAMPLE 47

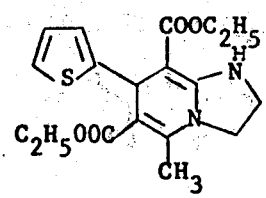

Boiling a solution of 7.4 g of then-2-ylideneacetoacetic acid ethyl ester and 5.2 g of 2-carbethoxymethylideneimidazolidine in 60 ml of ethanol for 6 hours yields 5-methyl-7-(thien-2-yl)-1,2,3,7-tetrahydroimidazolo[1,2-a]pyridine-6,8-dicarboxylic acid diethyl ester of melting point 134°C (ethanol).

Yield: 72% of theory.

EXAMPLE 48

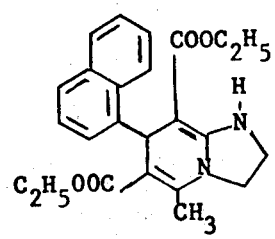

Heating a solution of 9.0 g of (naphth-1-ylidene)-acetoacetic acid ethyl ester and 5.2 g of 2-carbethoxymethylideneimidazolidine in 60 ml of ethanol for 6 hours yields 5-methyl-7-(naphth-1-yl)-1,2,3,7-tetrahydroimidazolo[1,2-a]pyridine6,8-dicarboxylic acid diethyl ester of melting point 169° – 170°C (ethanol).

Yield: 52% of theory.

What is claimed is:
1. A compound of the formula:

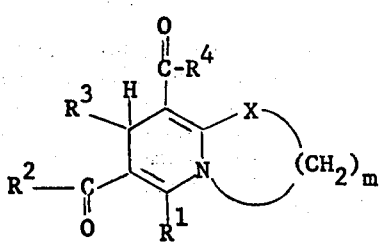

wherein
X is —CH$_2$—;
m is 3;
R$^1$ is hydrogen or lower alkyl;
each of R$^2$ and R$^4$, independent of the other, is lower alkoxy or alkynyloxy of 2 to 4 carbon atoms; and R³ is lower alkyl; phenyl; phenyl substituted by one to three substituents selected from the group consisting of lower alkyl, trifluoromethyl, cyano, halo, nitro and carbo(lower alkoxy); pyridyl; furyl; thenyl; or naphthyl.

2. A compound according to claim 1 of the formula:

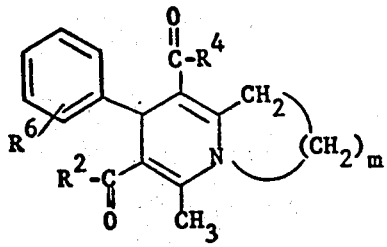

wherein
m has a value of 3;
each of R² and R⁴, independent of the other, is methoxy or ethoxy, and
R⁶ is nitro, cyano or trifluoromethyl in the 2- or 3- position of the depicted phenyl ring.

3. A compound according to claim 1 wherein each of R² and R⁴ is lower alkoxy and R³ is lower alkyl, phenyl or phenyl substituted by lower alkyl, trifluoromethyl, cyano, halo, nitro or carbo(lower alkoxy).

4. A compound according to claim 3 wherein R³ is methyl, phenyl or phenyl substituted by methyl, trifluoromethyl, cyano, chloro, nitro or carbethoxy.

5. A compound according to claim 1 wherein R² and R⁴, independent of the other, is methoxy or ethoxy; and R³ is methyl, phenyl or phenyl substituted by methyl, trifluoromethyl, cyano, chloro or nitro.

6. The compound according to claim 1 which is

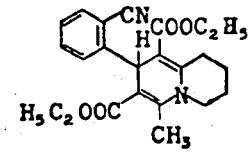

7. The compound according to claim 1 which is

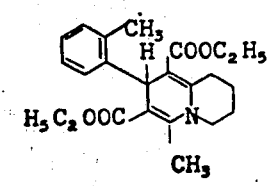

* * * * *